United States Patent [19]
Conway et al.

[11] Patent Number: 6,102,929
[45] Date of Patent: Aug. 15, 2000

[54] PROSTATIC TISSUE EXPANDER

[75] Inventors: Christopher J. Conway, Santa Barbara, Calif.; Terence M. Fogarty, Hudson, Wis.

[73] Assignee: Mentor Urology, Inc., Santa Barbara, Calif.

[21] Appl. No.: 08/791,514

[22] Filed: Jan. 30, 1997

Related U.S. Application Data

[63] Continuation of application No. 08/306,778, Sep. 15, 1994.

[51] Int. Cl.$^7$ .................................................. A61M 29/00
[52] U.S. Cl. ........................................... 606/192; 606/198
[58] Field of Search .............................. 606/192; 604/54, 604/96, 101, 102

[56] References Cited

U.S. PATENT DOCUMENTS

| | | | |
|---|---|---|---|
| 3,566,874 | 3/1971 | Shephard | 604/265 |
| 4,217,889 | 8/1980 | Radovan et al. . | |
| 4,267,829 | 5/1981 | Burton et al. . | |
| 4,643,733 | 2/1987 | Becker . | |
| 4,651,721 | 3/1987 | Mikulich et al. . | |
| 4,660,560 | 4/1987 | Klein . | |
| 4,718,410 | 1/1988 | Hakky . | |
| 4,881,530 | 11/1989 | Trick . | |
| 4,932,958 | 6/1990 | Reddy et al. . | |
| 5,002,558 | 3/1991 | Klein et al. . | |
| 5,007,898 | 4/1991 | Rosenbluth et al. . | |
| 5,030,227 | 7/1991 | Rosenbluth et al. . | |
| 5,159,920 | 11/1992 | Condon et al. . | |
| 5,499,994 | 3/1996 | Tihon et al. | 606/192 |

OTHER PUBLICATIONS

"Outpatient Transurethral Balloon Urethroplasty" by Douglas G. Travis et al.; N.Z. J. Surg. 1991, 61, 511–515.
"Balloon Dilation of the Prostate: Effective Treatment or Dilatory Tactic?", Howard M. Pollack, M.D., from the Department of Radiology, Hospital and Medical School of the University of Pennsylvania, 1991.
"The Devil in Dr. Pollack:Defending Our Souls", Neil F. Wasserman, M.D., from the Department of Radiology, Veterans Adminstration Medical Center, 1991.
"Balloon Dilation of the Prostate: Technique and Early Results", P.F. Keane et al., British Journal of Urology (1990) 65,354–356.
*The BPH Spectrum,* William G. Moseley, M.D., vol. 1, No. 2, "Seeing is Knowing".
"Transcystoscopis Balloon Dilatation of the Prostate", Lester A. Klein, MD, *Current Surgical Techniques in Urology,* vol. 3, Issue 3, pp. 1–8.
"Bladder Outflow Tract Obstruction and Urinary Retention from Benign Prostatic Hypertrophy Treated by Balloon Dilatation", K.P. Gill et al., British Journal of Urology (1989) 64, 618–622.
"Randomized Double–Blind Study Comparing the Effectiveness of Balloon Dilatio of the Prostate and Cystoscopy for the Treatment of Symptomatic Benign Prostatic Hyperplasia", Herbert Lepor et al., Journal of Urology, vol. 147, 639–644, Mar. 1992.
"Experimental Treatment of Benign Prostatic Hyperplasia with Transurethral Balloon Dilation of the Prostate: Preliminary Study in 73 Humans", Neil F. Wasserman, M.D. et al.
Product Chart: ASI Uroplasty TCU System Procedure Chart, Advanced Surgical Intervention, Inc., 1989.
Brochure: Freedom Leg Bag Systems, Mentor Urology, Jul. 1992.
Brochure: ASI Uroplasty TCU Prostatic Dilatation Catheter, Instruction for Use, Advanced Surgical Intervention, Inc. 1990.
"Dilatation of the Prostatic Urethra with 35 mm Balloon", J. McCloughlin et al., British Journal of Urology (1991) 67, 177–181.

*Primary Examiner*—Michael Buiz
*Assistant Examiner*—Daphna Shai
*Attorney, Agent, or Firm*—Fish & Richardson P.C., P.A.

[57] ABSTRACT

A prostatic tissue expander and method for treating benign prostatic hypertrophy comprising a flexible catheter having a distensible tissue expansion balloon, an inflatable Foley balloon at the distal end, a urine lumen, balloon inflation lumens and valves at the ends of the balloon inflation lumens for maintaining balloon inflation.

22 Claims, 5 Drawing Sheets

PROSTATIC TISSUE EXPANDER

This is a continuation of application Ser. No. 08/306,778 filed on Sep. 15, 1994 by the inventors named herein, and the benefit of priority under 35 USC §120 from that copending parent application is hereby claimed.

BACKGROUND OF THE INVENTION

This invention relates to medical tissue expansion, and more particularly it pertains to a prostatic tissue expander balloon catheter for expanding the prostatic urethra over a period of time. Inflation balloon pressure is maintained by valves in the inflation lumens. The tissue expander catheter is used to expand the prostatic urethra for the treatment of BPH (Benign Prostatic Hypertrophy).

By far the most common prostate problem is enlargement of the gland, or BPH. Common in men over 50, it is simply excess growth in the innermost part of the prostate. The urethra that empties the bladder runs through the middle of the prostate. The more the prostate enlarges, the more the flow of urine is constricted, causing a variety of uncomfortable symptoms when one tries to urinate.

The surgical solution to prostate enlargement has become the most common surgery confronting adult males today. It is known as Transurethral Resection of the Prostate (TURP). The Transurethral Resection procedure is carried out through a narrow tube-like instrument called a resectoscope, which is inserted into the urinary canal via the penis. Working through the resectoscope, the urologist carves out a portion of the prostate to enlarge the urinary passageway.

A recent alternative to TURP prostate surgery is the use of a small balloon, temporarily inserted into the urinary canal, precisely positioned where the urethra passes through the prostate, then inflated (for just minutes usually) to enlarge the urinary passageway where it is constricted by the enlarged prostate. During the 1980's, this concept in a different procedure won wide acceptance among cardiologists, who use a tiny balloon catheter to enlarge clogged blood vessels through a procedure called "angioplasty". In the case of the prostate, the procedure is known as "transcystoscopic urethroplasty". It is the urethra (not an artery) that is blocked, and it is the flow of urine (not blood) that is obstructed.

The Optilume Prostate Balloon Dilator manufactured by American Medical Systems is a dilator of the foregoing type for use in transcystoscopic urethroplasty. It has a non-distensible, single size, dilation balloon (diameter: 30 mm [90 Fr], length: 80 mm) located near the tip of a catheter shaft. A transparent locating balloon is mounted proximal to the dilation balloon. The balloons are enclosed in a PTFE sheath for placement in the urethra. This type of dilator is more fully described in U.S. Pat. Nos. 4,932,956 and 4,932,958 to Ready.

The sheath enclosed catheter of the dilator is inserted into the urethra. The balloons are moved out of the sheath and into working position with the locating balloon in the bulbous urethra, resting against the external sphincter. Positioning is accomplished by palpation, fluoroscopy or by placing a rod lens along side of the PTFE sheath and looking through the transparent locating balloon to confirm that the dilation balloon is in the proper location. The dilation balloon is inflated up to 60 PSI for 10 to 15 minutes, after which both balloons are deflated. The catheter is then drawn back into the sheath and removed.

In order to improve the removal characteristics, and thereby increase patient comfort, the dilator utilizes a PET balloon design which has a layer of silicone over the PET balloon with a coating of lubricant between the layers. The smooth finish and the elastic properties of the silicone permit easier removal of the deflated balloon.

Another known device is the Dowd catheter manufactured by Microvasive, Inc., which also has a non-distensible dilation balloon measuring 30 mm in diameter and 85 mm in length. A palpation nodule is mounted proximal of the balloon near the proximal end of the shaft. A knob is affixed to the shaft to provide a means of maintaining the position of the balloon during inflation. In use, the Dowd catheter is manually inserted without benefit of introducers or other sheaths. Throughout the entire procedure, the physician has a finger in the rectum against the nodule to judge positioning of the catheter. The balloon is inflated up to 60 PSI for the duration of the 10 to 15 minute procedure. During this time the urologist must maintain traction of the shaft to prevent the balloon from migrating into the bladder. The balloon is removed following deflation by twisting and pulling.

Another known device is the Uroplasty TCU design manufactured by Advanced Surgical Intervention. It features a Foley Balloon at its distal tip and a non-distensible dilation balloon mounted just proximal to the Foley balloon. The dilation balloon has a diameter of 25 mm (75 Fr), and is available in lengths from 15 mm to 55 mm.

A special "calibration" catheter with distance graduations on its shaft is inserted through a disposable introducer sheath which contains a rod lens for viewing the graduation adjacent to the sphincter. The calibration catheter is removed and a dilation catheter having the proper length balloon is installed. The Foley balloon on the dilation catheter is inflated in the bladder and exact placement is confirmed through the lens. The dilation balloon is inflated at up to 45 PSI for 10 to 15 minutes. Migration is not possible because the catheter is anchored by having one balloon on each side of the bladder neck. Upon deflation, the balloon is removed by withdrawing it through the introducer sheath thereby preventing further trauma to the urethra. Rosenbluth, U.S. Pat. Nos. 5,007,898 and 5,030,227, and Klein U.S. Pat. Nos. 4,660,560 and 5,002,558 describe such devices and are incorporated herein by reference in their entirety.

Balloon dilation of the prostatic urethra may produce a commissurotomy or tearing, which is considered by some to enhance the results. Bleeding frequently accompanies the procedure. A catheter may be placed immediately following the dilation to allow the patient to void comfortably. Unfortunately, it has been found that the beneficial results from treatment as mentioned above are fairly short lived for the balloon dilation procedure.

As noted above, transcystoscopic urethroplasty (TCU) or transurethral balloon dilation of the prostate (TUDP) can and in many cases does rupture the urethra (commissurotomy). Even so, the progressive development of this technique has tended toward the use of larger and larger diameter dilation balloons. See the paper entitled "Dilation of the Prostatic Urethra with 35 mm Balloon" by McLaughlin et al., which appeared in the BRITISH JOURNAL OF UROLOGY (1991), 67, 177–181.

A procedure known as tissue expansion is also known in the medical art. In tissue expansion procedures, a temporary device for expanding or stretching skin and tissue is placed within the body and is expanded over an extended period of time and left in place until the tissue or skin stabilizes to an enlarged and permanent size. This procedure is used to treat burn victims and for breast reconstruction. See U.S. Pat. Nos. 4,643,733 and 4,217,889 for example. No one to date has thought to apply the concept of tissue expansion to the TCU or TUDP procedure, utilizing a distensible balloon, as a substitute for the presently practiced procedure utilizing short time balloon dilation with a non-distensible balloon.

SUMMARY OF THE INVENTION

In summary, this invention provides means, including a distensible balloon, for applying tissue expansion to the alleviation of obstructive prostatism. The invention may be expressed in terms of both an apparatus and a method. Tissue Expansion as used in this invention relates to relatively long term gradual expansion, preferably applied in gradual steps over a period of time, to stabilize tissue growth. On the other hand dilation as used in the prior art relates to short term somewhat drastic expansion and is readily distinguished from this invention.

This invention offers several advantages over the prior art including the following:

Dilation balloon devices traumatically and temporarily dilate the prostatic urethra with mixed results reported over the short term (up to 18 months). Long term results are unavailable but expectations are low. On the other hand, the tissue expansion approach of the present invention, occurring over an extended period, which allows physiological compensation and tissue generation, should yield good long term results.

Tissue expansion is less traumatic and inherently requires less volumetric displacement than dilation.

The expansion and expansion rate of the prostatic urethra in accordance with the tissue expansion approach of this invention is based on patient comfort and tolerance. A commissurotomy can be avoided and instead tissue expansion will occur. When full expansion is achieved the tissue expander may be left in place for a few days to stabilize the tissue expansion.

There has been noted in other devices, some tendency for a dilation balloon to migrate into the bladder. In some cases, damage to the sphincter or bladder neck has been reported leading to incontinence and retrograde ejaculation. The tissue expansion technique minimizes the potential for such problems.

The procedure is an out-patient one versus a hospital procedure.

A choice of multiple balloon sizes will accommodate individual anatomy.

The use of a sheath or introducer is not required.

Distensible balloons as suggested for use in this invention increase in size in proportion to the inflation pressure and shrink or constrict approximately to their original shape upon deflation; non-distensible balloons as used in the prior art are of fixed surface area (the envelope does not readily shrink on deflation) and can cause trauma upon removal.

Significant features of this invention are as follows. Tissue expansion is minimal and may take place at a gradual rate. In the previous applications of balloon dilation catheters for the treatment of BPH, the balloon was inflated for only a short time. The longest period of dilation suggested is described in the Klein U.S. Pat. No. 5,002,558, abstract and line 30 of Column 6, as a period of "one hour or more". The present invention teaches that inflation extending over much longer periods, perhaps days or even weeks, should be used to accomplish tissue expansion. This gradual expansion, which is accomplished by adding small amounts of the expanding solution to the balloon over a period of time, minimizes discomfort. When the procedure is completed, the prostatic urethra has been enlarged, with relief of the symptoms of BPH without significant trauma.

BRIEF DESCRIPTION OF THE FIGURES

Various objects of the present invention and many of its attendant advantages will be more readily appreciated by reference to the following detailed description when considered in connection with the accompanying drawings, in which like reference numerals designate like parts throughout the Figures thereof and wherein.

DETAILED DESCRIPTION OF THE PREFERRED EMBODIMENTS

Figures 1, 2A, 2B, 2C:
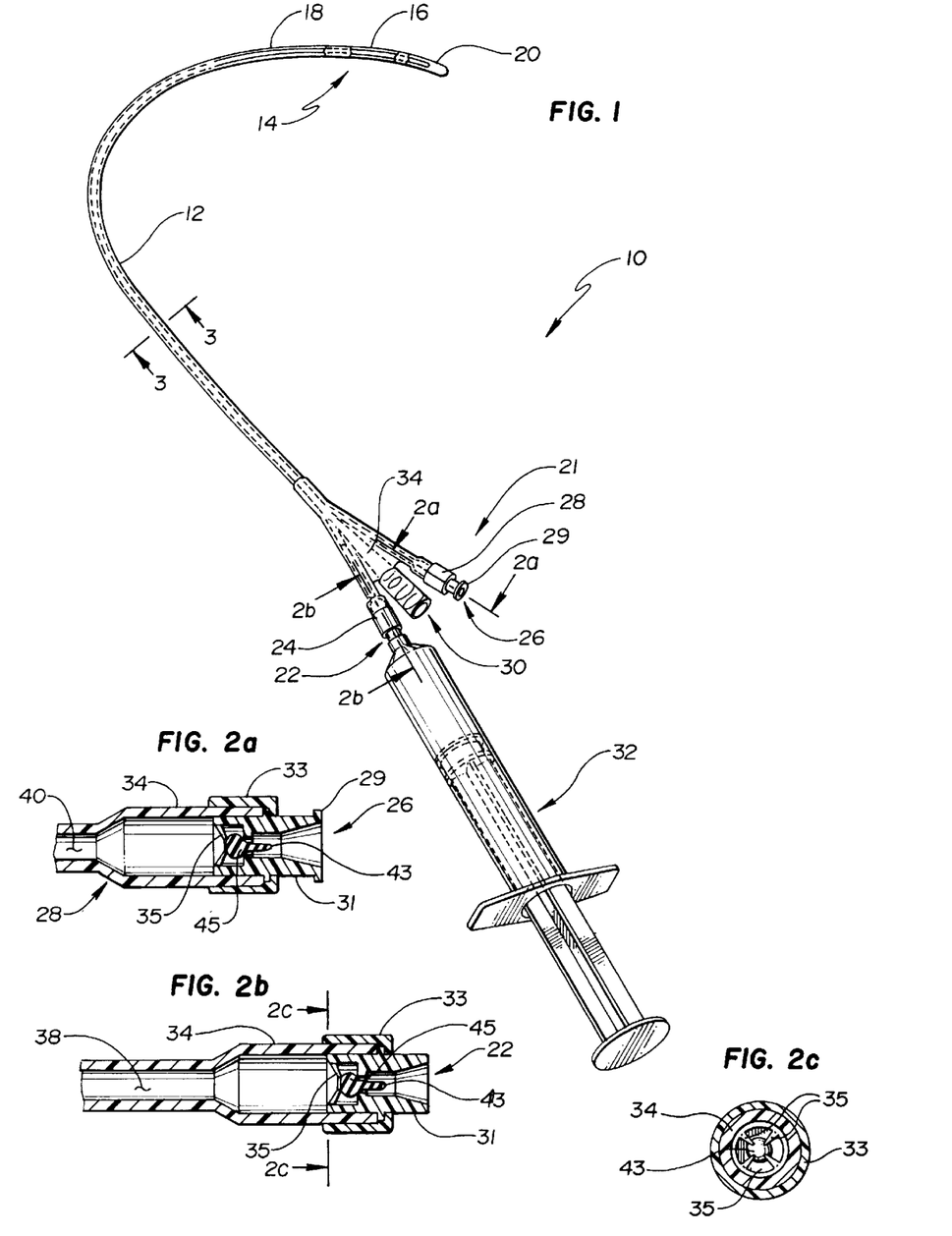
FIG. 1 illustrates a perspective view of a prostatic tissue expander according to the present invention.
FIGS. 2a and 2b are longitudinal cross-sectional views of the valves 24 and 28 taken along lines 2a—2a and 2b—2b, respectively in FIG. 2.
FIG. 2c is a cross-sectional view of the 2b valve taken along line 2c—2c in FIG. 2b.

The preferred prostatic tissue expander of this invention as illustrated in FIG. 1 includes two inflatable balloons: A first positioning balloon, preferably a Foley balloon, located at the distal tip and a second balloon, a distensible tissue expansion balloon, located proximal of the first balloon. Preferably, the tissue expansion balloon will be available in a range of lengths and sizes for each patient. Being distensible, the diameter of the tissue expansion balloon increases as internal pressure is raised by inflation. The catheter shaft upon which the balloons are mounted is of a flexible material and may be reinforced in the region of the tissue expansion balloon to prevent occlusion of the catheter lumens, if required. The catheter shaft of this embodiment is equipped with two lumens to connect the balloons to pressure retaining valves located at the proximal end of the device. A center lumen is also provided having a proximal connector to attach to a urine collection device, such as a leg bag.

Insertion of the device into the urethra is similar to the procedure used with a standard Foley catheter: The shaft is lubricated and manually inserted until the distal tip is in the bladder. The positioning balloon is inflated and mild traction is applied while the tissue expansion balloon is partially inflated. With both balloons inflated, the device is anchored in place. Since no part of the second balloon is in the bladder, there is no tendency of the device to migrate into the bladder. Inflation of the second balloon may be increased gradually over a period of days or weeks to effect tissue expansion. After the expansion reaches a desired level, the balloon may be left in place while the prostate adjusts to the increased size of the urethra and establishes tissue stability. Upon completion of the treatment, the balloons are deflated and returned to their original diameter, approximately that of the device shaft. The device is then withdrawn from the urethra.

Referring now to FIG. 1 in detail, there is shown a perspective view of a prostatic tissue expander, generally indicated at 10, including a plastic, lumened catheter shaft 12, a distal end generally indicated at 14 having a Foley balloon 16, a distensible tissue expander balloon 18, and a urine port 20. The proximal end of the prostatic tissue expander 10, generally indicated at 21, includes a Foley balloon inflation port generally indicated at 22 and an associated inflation control valve 24, a distensible tissue expander balloon inflation port generally indicated at 26, an associated inflation control valve 28, and a connector generally indicated at 30 for coupling the device to a urine collection bag (not shown). An inflation syringe generally indicated at 32 may be used to inflate the Foley balloon 16 as shown and the distensible tissue expander balloon 18 by connection to the proper inflation port 22 as shown or 26 by means of, for example, Luer fittings. Such fittings are well known in the art.

Valves 24 and 28 may in the most basic form of this invention be simple manual "off" "on" valves for selectively inflating and deflating the balloons. Optional valving arrangements may be used if desired and preferred valves are described fully hereinbelow.

Catheter shaft 12 is formed of a material which is flexible enough to follow the bends in the urethra on insertion of device 10. The material should be rigid enough, however, to allow device 10 to pass over any obstructions within the urethra. Catheter shaft 12 may be composed of or covered by a biocompatible material to avoid irritation and complication in the urethra. Such catheters and covering materials are well known in the art. Suitable biocompatible materials which may be made into lumened tubing of suitable flexibility and rigidity for shaft 12 are, for example, silicone, latex, polyvinylchloride and polyurethane, silicone presently being most preferred.

Balloon 16, the positioning balloon, is formed of a biocompatible material such as silicone or C-Flex, a styrene ethylene butylene styrene modified block copolymer, and is preferably of the Foley type.

Balloon 18, the distensible tissue expanding balloon, is also formed of biocompatible low modulus elastomer material such as latex, silicone or C-Flex, being of the distensible type its diameter can be varied on inflation over a range of diameters. Distensible balloon construction is known in the art and need not be described here in detail. In some instances, balloons of controlled distensibility may be desired and in such instances a high modulus elastomer such as polyurethane may be used or reinforcement may be incorporated into a balloon of low modulus elastomer in accordance with known techniques.

Figures 2, 3:
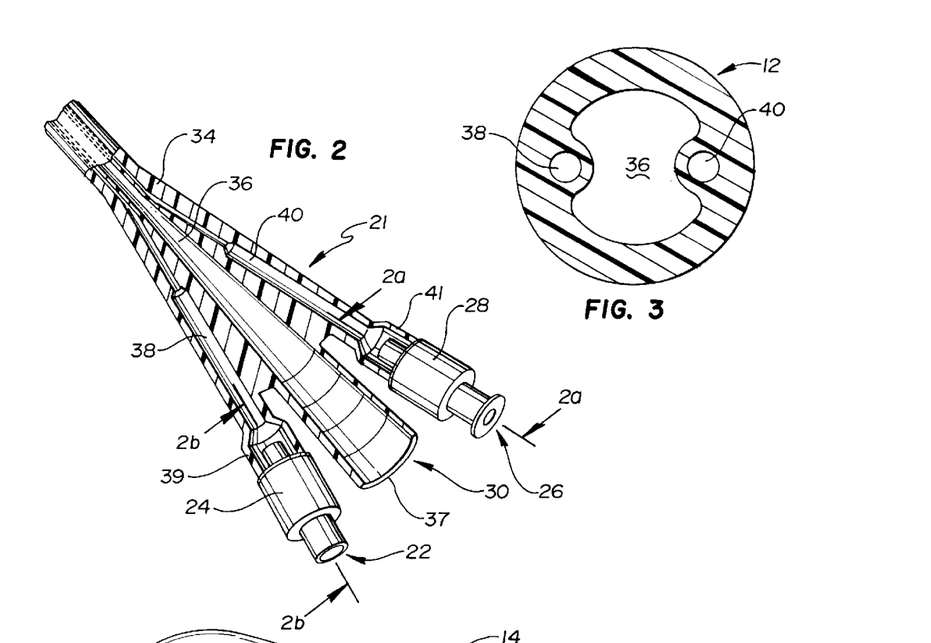
FIG. 2 illustrates a partially broken away longitudinal cross-sectional view of a major portion of the proximal end of the tissue expander catheter of FIG. 1.
FIG. 3 illustrates a cross-sectional view of the catheter shaft taken along line 3—3 of FIG. 1.

Reference is now made to FIG. 2 which shows a cross-sectional view of the major portion of the proximal end generally indicated at 21 of the tissue expander 10 taken along line 2—2 of FIG. 1 in which all numerals correspond to those elements previously described. Proximal end 21 includes a branched body 34 having a central urine drainage lumen 36 flanked by lumens 38 and 40, all of which extend longitudinally through the catheter shaft 12 of FIG. 1. Urine drainage lumen 36 is a requisite feature of the device since the device is in place over a period of time extending from days to weeks and provision must be made for urination during that extended time. Lumen 38 terminates proximally in a funnel-like end portion 39 and interconnects the positioning balloon 16 inflation port 22 and inflation control valve 24 (see FIGS. 1 and 2) to positioning balloon 16 through a balloon port 44 (seen in FIGS. 4 and 5). Lumen 40 connects the distensible tissue expander balloon inflation port 26 and inflation control valve 28 (see FIGS. 1 and 2) to the distensible tissue expander balloon 18 through a balloon port 48 (seen in FIGS. 4 and 5). Lumens 38 and 40 likewise may terminate in funnel-like branched end portions 39 and 41 respectively.

Valves 24 and 28 are shown in a preferred construction in FIGS. 2b and 2a, respectively and in 2c. Valve 24 is shown with a standard tapered Leur fitting by means of which the syringe pump of FIG. 1 is attached to port 22, as is known in the art. Because the attachment is of relatively short duration, this arrangement is considered to be satisfactory although not critical. On the other hand, valve 28 includes a hub fitting 29, another standard Leur fitting known in the art, because a pump (as will be described further hereinbelow) is attached to port 26 for long term association with the device. In other respects, the two valves 24 and 28 are essentially identical and include the same elements, all of which are preferably formed of any suitable thermoplastic. Many specific materials will be readily apparent to those familiar with the medical device art, including materials other than thermoplastics.

Both valves include valve bodies 31, a retainer 33 which holds the valve body in place as shown in the respective branch of body 34. Valve bodies 31 respectively define the inflation ports 22 or 26 and contain a flexible multi-fingered valve actuator retainer 35 and valve actuator rod 43. Actuator rod 43 seats against seat 45 to normally close the valve and is held in place normally by actuator retainer 35 as shown. When a syringe or other device is inserted into the respective port 22 or 26 and pushes against actuator rod 43 it is moved against the bias provided by the actuator retainer 35 to move away from seat 45 thus opening the valve.

FIG. 3 illustrates in cross-sectional view the lumened catheter shaft 12 taken along line 3—3 of FIG. 1 where all numerals correspond to those elements previously described. Illustrated in particular are the inflation lumens 38 and 40 flanking the central urine drainage lumen 36.

Figure 4:
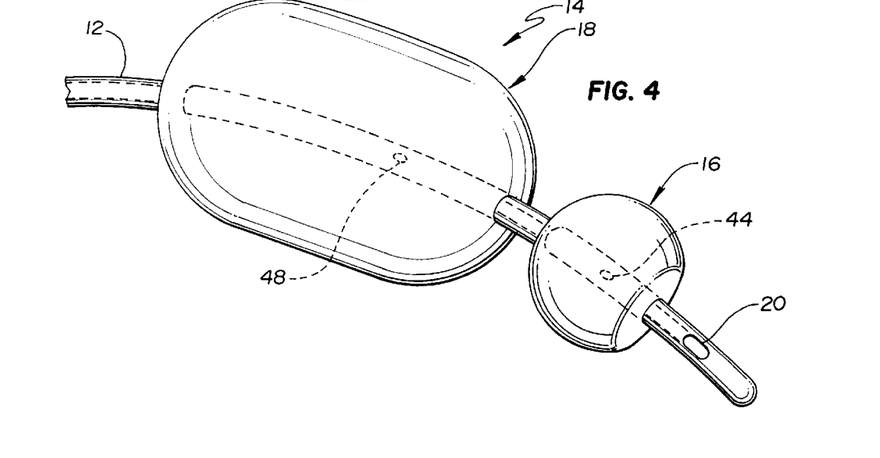
FIG. 4 illustrates the inflation of the balloons of the tissue expander shown in FIG. 1.

The inflated distensible tissue expander balloon 18 and the positioning balloon 16 at the distal end 14 of the prostatic tissue expander 10 is illustrated in FIG. 4 where all numerals correspond to those elements previously described.

Figure 5:
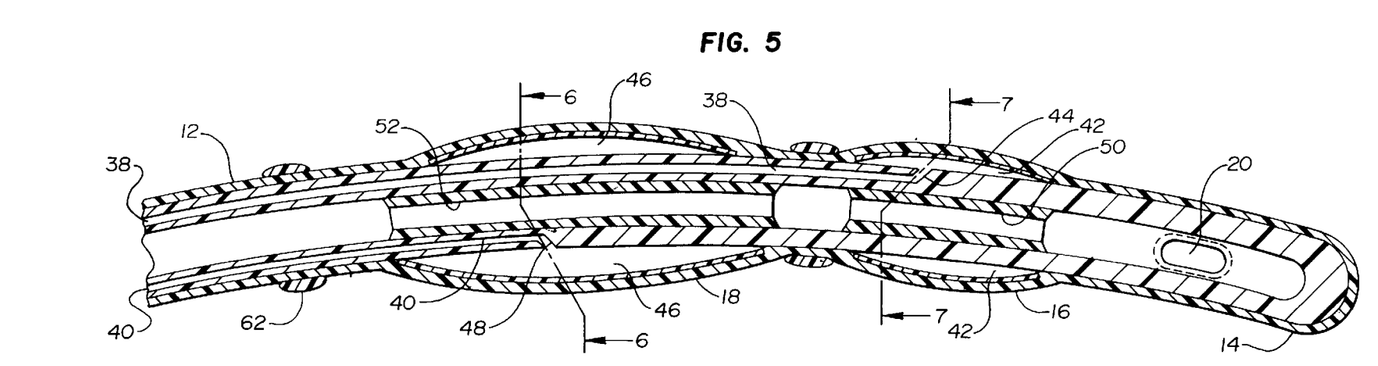
FIG. 5 illustrates a longitudinal sectional view of the distal tip of the catheter taken along line 5—5 of FIG. 1 and includes a palpated nodule 62 on the catheter shaft.
Figure 6:
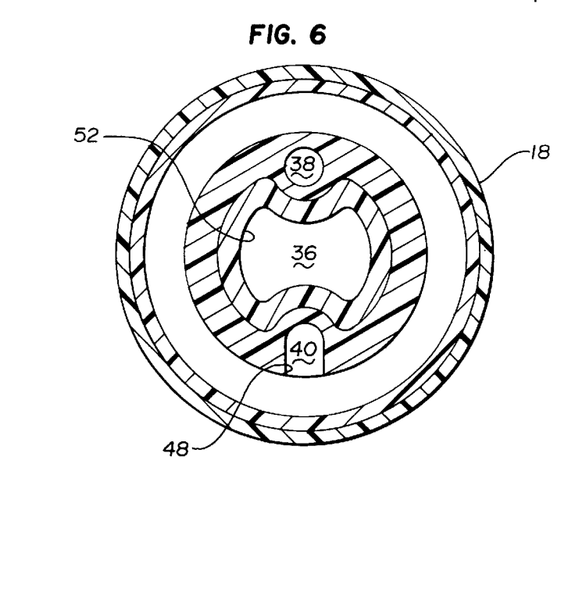
FIG. 6 is a cross-sectional view along line 6—6 of FIG. 5.
Figure 7:
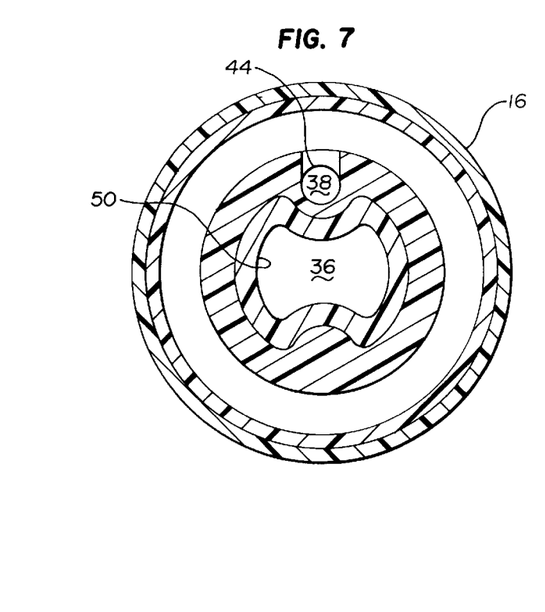
FIG. 7 is a cross-sectional view along line 7—7 of FIG. 5.

Reference to FIGS. 5, 6 and 7 provides an illustrated sectional views of the distal tip portion 14 of tissue expander 10. In FIG. 5 the cross-section is taken longitudinally and parallel to line 5—5 of FIG. 1 in which the positioning balloon 16 and the distensible tissue expander balloon 18 are slightly expanded and in which all numerals correspond to those elements previously described. In FIG. 6 the cross-section is taken along line 6—6 in FIG. 5 of the partially inflated distensible tissue expander balloon 18 of FIG. 5 in which all numerals correspond to those elements previously described. In FIG. 7 the cross-section is taken along line 7—7 of the partially inflated Foley balloon 16 of FIG. 5 where all numerals correspond to those elements previously described. Illustrated in particular is a reinforcement tube 50 located in the urine lumen 36.

In these FIGS. 5–7 the positioning balloon 16 (preferably the Foley type) and distensible tissue expander balloon 18 are shown bonded to or otherwise suitably secured around and about the lumened catheter shaft 12 in communication with their respective balloon ports 44 and 48. Inflation lumen 38 is ported to the interior 42 of the positioning balloon 16 by port 44. Inflation lumen 40 is ported to the interior 46 of the distensible tissue expander balloon 18 by port 48. Optional reinforcement tubes 50 and 52, having interior lumen passageways 50a and 52a respectively, are located and suitably secured in the urine lumen 36 within the Foley balloon 16 and the distensible tissue expander balloon 18, respectively. These may be of a higher modulus elastomer, a thermoplastic or metal. Pressure by fluid flow through the lumens is exerted against the inner walls of balloons 16 and 18 to expand the balloons. Pressure is also exerted inwardly upon the exterior of lumened catheter shaft 12. Reinforcement tubes 50 and 52 prevent closing of the urine path by pressure exerted upon the exterior of the lumened catheter shaft 12 and extend proximally from urine port 20 along urine lumen 36. Thus, a continuous urine passageway, including the urine lumen 36 and interior lumen passageways 50a and 52a is maintained during any state of balloon inflation. Other arrangements for achieving this end will be apparent to those familiar with the catheter art.

Also, a locating nodule 62 as earlier referred to may be included on catheter shaft 12 as shown in FIG. 5 and as is known in the art.

As can be seen from the preceding description, one basic embodiment of the invention comprises the following elements:

A. Tip with drainage eyelet(s)—14 and 20;
B. Positioning balloon—16;
C. Expander balloon—18;
D. Triple lumen catheter shaft—12;
E. Urine drainage funnel—37;
F. Inflation valve, positioning balloon—24; and,
G. Inflation valve, expander balloon—28.

The following dimensional information will aid in understanding the construction of a tissue expander device.

A. Tip with drainage eyelet(s)—14 and 20: The tip or distal end 14 and catheter tube or shaft is preferably between about 12–30 French, and preferably about 14–18 French. The end of the tip is preferably radiused. The length of the tip, from the end of the tip to the positioning balloon is preferably about 30–40 mm. Drainage eyelets (orifices) 20 are preferably round, circular or oval in shape and should preferably not exceed the width of the drainage lumen. Eyelet size should preferably not be less than 2.5 times greater than, the cross-sectional area of the drainage lumen. Reference: British Standard (BS) 1965 Part 1 (incorporated herein in its entirety by reference).

B. Positioning balloon—16: The positioning balloon is preferably located about 30–40 mm from the end of the tip 14 and should not cover the drainage eyelets 20 when inflated. The balloon is preferably distensible and has a preferred shape which is a relatively symmetrical doughnut shape when inflated. The balloon has a preferred nominal inflation volume of about 5–30 ml. The balloon may be fabricated from latex, silicone, C-Flex or other distensible elastomer, preferably silicone and may include double layers as seen in FIGS. 5, 6 and 7. Uninflated, the balloon may be up to about 4 sizes French greater than the labeled shaft size, but preferably no greater than 1 French. The length of the uninflated balloon should be 1–2 cm, preferably about 1.5 cm. Reference: BS 1965 Part 1 and ASTM F 623 (incorporated herein in their entirety by reference).

C. Expander balloon—18; The expander balloon 18 should preferably be located about one-half centimeter or less from the positioning balloon 16. The shape of the expander balloon 18 is preferably cylindrical with the ends configured to enable expansion close to the external sphincter and the bladder neck. See U.S. Pat. No. 5,007,898 which is incorporated herein by reference for general guidance in this respect. The expander balloon is distensible or preferably exhibits controlled distensibility, unlike the prior art dilating devices which are non-distensible. The expander balloon 18 may be produced in various inflated lengths from about 15–75 mm. Inflated diameters of expander balloons with limited distensibility may range from about 10–30 mm (30–90 French). The expander balloon may be fabricated from elastomers such as C-flex, silicone, latex or other low modulus elastomers and may be comprised of double layers as seen in FIGS. 5, 6 and 7. Balloons with limited distensibility may be fabricated from higher modulus polyurethane or lower modulus elastomers in combination with reinforcing materials. Reinforcements of this type and limited distensibility are taught in U.S. Pat. Nos. 4,651,721, 4,718,410 and 4,881,530, all of which are incorporated herein by reference. For example, extensible polyurethane spandex filament may be wrapped with a non-extensible polyester filament and knitted into a reinforcing element which is embedded in a low modulus elastomer. Longitudinal pleated elements of non-distensible materials may also be used in combination with elastomeric membranes for expander balloons with controlled extensibility.

D. Triple lumen catheter—12: The triple lumen catheter 12 will preferably have a round or oval shape and range in size from about 12–30 French, preferably about 16 French. A major lumen 36 is provided for urine drainage and is preferably sized to yield a minimum flow rate of about 100 ml. per minute when tested per BS 1965 Part 1 or ASTM F-623. Two minor lumens 38 and 40 are provided for inflating the positioning and expander balloons. Preferably the cross-sectional area of the minor lumens is about 0.50–1.0 square mm., to afford a reasonably rapid balloon inflation rate.

A nodule 62 (FIG. 5) may be located on the shaft 8 mm or thereabouts proximal from the expander balloon. In this respect, reference is made to "Balloon Dilation of the Catheter", Joseph B. Dowd and John Smith, *Urologic Clinics of North America*, Volume 17, No. 3, August 1990 which is incorporated herein by reference. This nodule 62 may be used by the physician to assure that the expander balloon is not positioned in the external sphincter, i.e., the nodule may be palpated with the index finger through the rectum. To prevent occlusion of major lumen 36 at the balloons, reinforcement may be incorporated in the wall of the shaft. For example, a sleeve having higher modulus than the catheter shaft walls may be used to support the lumen and resist external forces on the shaft. This has already been referred to in connection with FIG. 5. The catheter shaft or tube 12 may be fabricated from latex, silicone, C-Flex, polyurethane, or other suitable elastomer. The preferred material is silicone.

E. Urine drainage funnel—37: The proximal end of the catheter shaft 12 terminates at the urine drainage funnel end portion 37 and the branched funnels 39 and 41 connected to the minor catheter lumens 38 and 40. The urine drainage funnel 37 is preferably the central funnel end portion because it connects to the major lumen 36. The funnel length is about 25–60 mm long and is preferably cylindrical, conical or a combination thereof. An appropriate connector joins the drainage funnel to a urine collection device (not shown). The material used for the funnel is preferably the same as the catheter shaft.

F. and G. Inflation funnels 39 and 41 and valves 24 and 28 for positioning and expander balloons 16 and 18: The branched funnels 39 and 41, preferably cylindrical, are used to connect the minor lumens 38 and 40 to the inflation valves 24 and 28. Thermoplastic medical inflation check valves 24 and 28 are secured to the branched funnels. The check valves have elastomeric seals and may have stainless steel springs. The valves preferably have a 6% female Luer taper per ANSI/HIMA MD 70.1 and BS3930 (incorporated herein by reference), and are operated with a medical syringe 32 or other pump having a 6% Luer taper (valve 28 including a hub as earlier described). A thermoplastic retainer sleeve may be fitted over the exterior surface of the funnel end portions to retain the valves. Valves and retainers of this type are available from Bespak Plc, of Norfolk, England. The branched funnels are preferably fabricated with the same materials as the catheter shaft.

The overall length of the tissue expander device is preferably about 380 mm (reference BS 1965 part 1).

The tissue expander device may include a hydrophilic surface which is bonded to the catheter shaft and balloons. Considerable prior art exists on composition and attachment of hydrogels and hydrophilic surface treatments to hydrophobic elastomers. This will already be known to those familiar with the medical device art.

Because indwelling catheters present a path for infection, a prophylactic antibiotic may be incorporated in the hydrophilic surface. Alternatively the antibiotic may be applied by the physician who would soak the expander in an antibiotic solution before placing it in the patient.

Following are examples of hydrogel surfaces and antibiotics which may be impregnated into them.

Hydrogel materials may be bonded to the surfaces of the balloons and shaft for greater patient comfort and reduced tissue irritation. The hydrogel may be impregnated and packaged with antibiotic agents. Alternately the physician may soak the hydrogel coated device in antibiotic prior to insertion.

The following are examples of hydrophilic (Hydrogel) materials:

| | |
|---|---|
| PHema | (Poly 2-Hydroxyethyl-methacrylate) |
| PVA | (Poly Vinyl Alcohol) |
| PEO | (Poly Ethylene Oxide) |
| NVP | (N, Vinyl-2-Pyrrolidone) |
| Cellulose Ethers | |
| Examples of Hydrophilic Copolymers are: | |
| NVP and Polyurethane | |
| NVP and PHema | |

-continued

Examples of Hydrophilic/Hydrophobic Copolymers are:

| | |
|---|---|
| NVP and MMA | (Methyl Methacrylate) |
| PHema and EMA | (Ethyl Methacrylate) |
| PHema and Hexanediol Mono Methacrylate | |

Copolymerization of hydrogels affords the opportunity to tailor the properties such as water content, processing characteristics, and physical properties in the unhydrated state. The time release characteristics for the release of antibiotics may also be tailored with copolymerization of the hydrogel surface component.

The following are examples of antibiotics which have obtained acceptance in the treatment of urinary tract infections, which may be incorporated into a hydrophilic surface:

Nitrofurantoins

Quinolones

Cephalasporins.

Combinations of more than one antibiotic may prove beneficial in controlling organisms that may develop resistance to extended exposure to a single antibiotic.

The expander will preferably be supplied sterile in a quadruple barrier package (not shown). A first microbial barrier package inside a second microbial barrier package would be placed in a shelf box which has a protective plastic shrink wrap. Sterilization may be accomplished using gas sterilant such as ethylene oxide, radiation such as electron beam or gamma, steam autoclave or dry heat.

TISSUE EXPANSION PROCEDURE

Sizing of the appropriate distensible balloon to be used in the procedure is done first. This may be accomplished as in the prior art by use of a calibration catheter which measures the distance between the bladder neck and the external sphincter within the prostatic urethra. The physicians may then select the tissue expander catheter of the invention whose distensible balloon length is closest to the measurement taken. A variety of sizes will be available for this selection.

Commercially, the expander balloon will be made available in different lengths to conform to the length of the prostatic urethra. Measuring the distance from the bladder neck to the bottom of the prostate gland has been previously described by Klein in U.S. Pat. No. 4,660,560 and Klein et al, in U.S. Pat. No. 5,002,558, both of which are incorporated herein by reference. The device of the present invention would preferably be accompanied by such a catheter to measure prostate length with a cystoscope as part of the commercial package. However, since it is well known it need not be described herein in detail.

The selected tissue expander catheter is inserted into the urethra with the aid of lubricating jelly or the like making sure that the positioning balloon and catheter tip have passed through the bladder neck and the expander balloon is positioned within the prostatic urethra.

Figure 8:
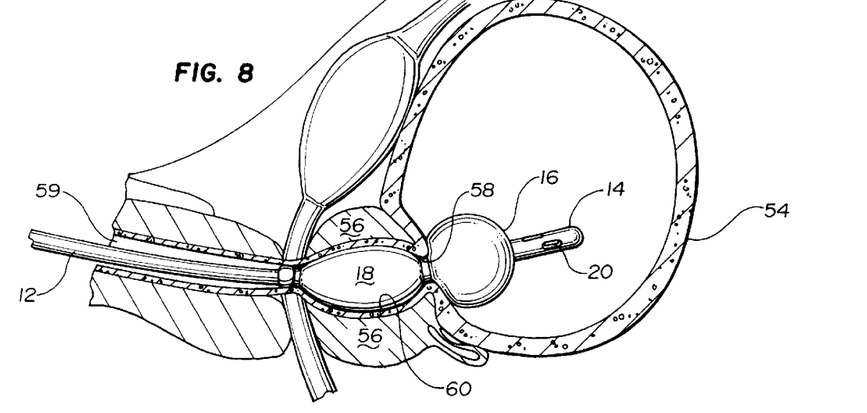
FIG. 8 illustrates the urethral placement of the distal tip, and the balloons of the tissue expander of the invention with respect to the bladder and the prostate gland.

FIG. 8 illustrates the placement of the tissue expander 10 including the distal tip 14 and associated components, including the positioning balloon 16 and the distensible tissue expander balloon 18 with respect to the bladder 54 and the prostate 56 through the urethra 59 of a male. Before insertion into the urethra, the balloons are in a completely deflated state and are collapsed against the tube 12. The inflation of both the positioning balloon 16 and at least the partial inflation of the distensible tissue expander balloon 18 anchors the distal tip 14 of the expander device to the bladder neck 58 at a point between the positioning balloon 16 and the distensible tissue expander balloon 18. The positioning balloon 16 remains entirely within the bladder 54 and the distensible tissue expander balloon 18 remains entirely within the prostatic urethra 60 within prostate 56. The distensible tissue expander balloon 18 is then slowly inflated as desired over a period of time to gradually increase the prostatic urethra to a desired size. Once the desired size is reached, the tissue expander may remain in place for a period of time to stabilize growth. Afterwards, the balloons are deflated by opening valves 24 and 28 and the expander device 10 is then withdrawn from the bladder and the urethra.

Generally speaking, it is anticipated that a maintenance pressure of about 2–5 psi will be adequate within the distensible balloon and a fluid inflation volume adequate to size the balloon within about 8–10 mm in diameter initially with gradual step-wise expansion to about 15–30 mm in diameter will be effective with the procedure of this invention. The procedure may extend over a period of days or even weeks. It is anticipated that about 3 weeks will be effective. During this time it will be necessary for the patient to wear a leg bag or the like which may be connected to port 30 for collection of urine.

FURTHER EMBODIMENTS

Up to this point the invention has been described with reference to a more basic embodiment thereof. In that embodiment, the physician installs the tissue expander and sees that patient periodically, perhaps once a day for example, to adjust the pressure and size of the distensible balloon as desired and otherwise inspect the device for proper positioning and the like.

In this basic embodiment the physician would inflate the expander balloon 18 and adjust intraluminal pressure using a syringe with pressure gauge to introduce sterile fluid through the check valve 28 attached to the proximal end of the expander. The patient would return to the physician periodically during the prostate tissue expansion period for expander fluid adjustments.

Figure 9:
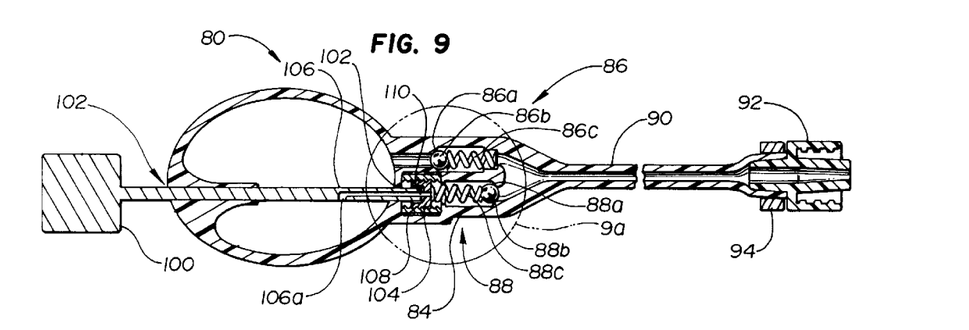
FIG. 9 shows an embodiment of a pump to be used with the catheter device of the invention.
Figure 9A:
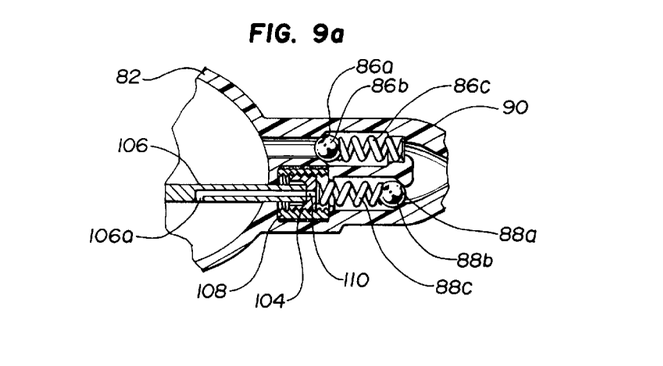
FIG. 9a is an enlarged view of a portion of the pump.
Figure 10:
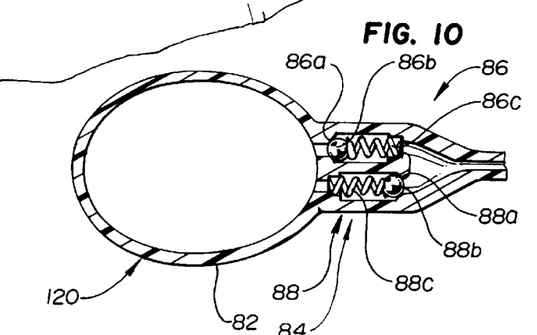
FIG. 10 shows a modified structure for the pump of FIG. 9.

However, a pump may be included with the device during the procedure and connected long term to the distensible balloon port 26. The pump may include a pressure regulator arrangement (as shown in FIG. 9) or the like for the physician to adjust the pressure or it may be preset to regulate a predetermined pressure within the balloon (as shown in FIG. 10). Such versions are now described hereinbelow.

Patient Pump With Optional Features (FIG. 9)

The first mentioned further embodiment offers a patient pump 80 with optional features which is similar to the basic embodiment except that pump 80 includes a means (shown in FIG. 9) for the physician to adjust the pressure at which the regulating pump valve 88 opens. The physician uses a Luer adapter to connect a syringe 150 (see FIG. 11) and pressure gauge 160 to the pump. An optional adjusting tool 100 is inserted through an optional access port 102 and engaged with an optional pressure adjusting set screw 104. The surgeon uses the syringe to create back pressure on the pump tubing 90 and valve 88. The gauge attached to the syringe will indicate the pressure at which the regulating valve 88 is set. Excess fluid will vent from the pump bulb along the optional fluid path 106 between the access port 102 in the pump bulb 82 and the adjustment tool 100.

The following optional components (all shown in FIG. 9), distinguish the pump as modified for this embodiment.
Threaded bushing—108

The chamber housing valve 88 also contains the internally threaded bushing 108. The bushing may be metal or thermoplastic and is bonded to the chamber. The bushing thread must be large enough to accommodate the spring. For a 0.125" spring diameter, a #8-32 UNF thread is used. The bushing length is adequate to house the set screw and to allow for advance or withdrawal of the screw to achieve the anticipated pressure range. For example with a 0–10 psi range the bushing would be approximately 0.38" in length.
Adjustment Set Screw—104

The socket head adjustment screw 104 is fabricated from metal or thermoplastic and has a thread compatible with the bushing 108. The set screw is advanced or withdrawn to lengthen or shorten the chamber length available for the compression spring 88c. Varying the chamber length varies the preload of spring 88c and changes the pressure setting of regulating valve 88. Adjustment screw 104 has through hole 110 in it so fluid may pass through the screw during adjustment. A thermoplastic insert (not shown) may be set in a recess located in the threads to prevent rotation below the torque that is available with the adjustment tool 100.
Pressure Adjustment Tool—100

A metal or thermoplastic adjustment tool 100 in the form of a hex shaft with a finger grip is provided. The adjustment tool engages adjustment screw 104 so that it can be rotated for pressure adjustment.

The end of the tool shaft which engages the set screw contains a fluid passage 106 which terminates at a cross hole 106a on the tool shaft. The purpose of this fluid channel 106 is to allow fluid to escape the valve during adjustment without having to remove the tool.
Access Port—102

The pump bulb contains access port 102, through which the adjustment tool 100 is passed to engage set screw 104. This may be a simple aperture and plug or a duckbill-type valve that is configured to resist opening with negative pump bulb pressures. A leaf-type valve of the type used in inflatable mammaries, Ref. U.S. Pat. No. 4,782,826 incorporated herein by reference may also be used.

Figure 11:
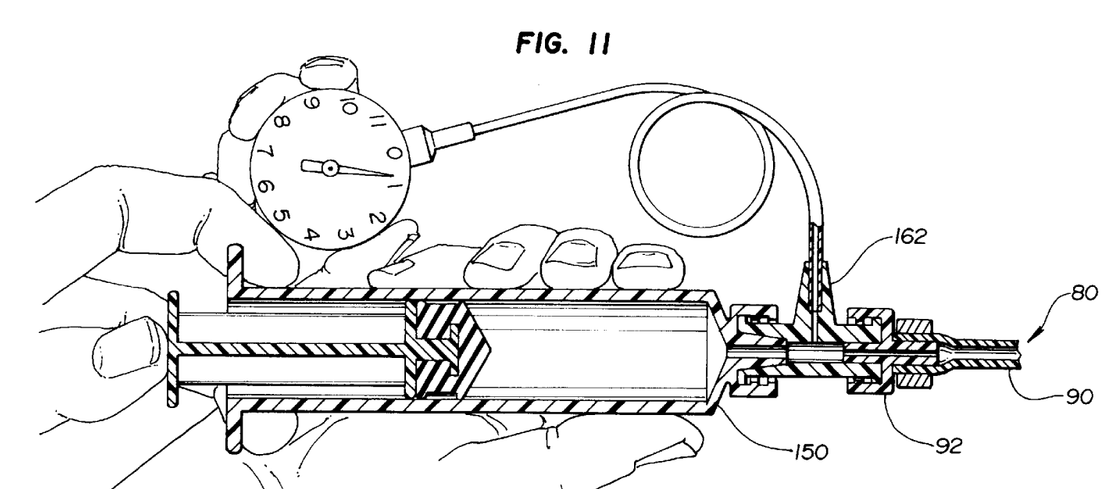
FIG. 11 shows a syringe with pressure indicator for use with the pump of FIG. 9.

The pump and syringe both have a male Luer Lock fitting as can be seen in FIG. 11, respectively.

A Female Luer adapter 162 (see FIG. 11) is provided to connect the syringe 150 and gauge 160 to the pump in order to adjust the pressure of regulating valve 88.

The adapter may be metal or thermoplastic. The fitting is fabricated with 6% female Luer tapers on both ends to engage the syringe and pump Luer. Luer hubs are optional.
The Preset Patient Pump (FIG. 10)

In a preset pump embodiment (FIG. 10) the physician inflates the expander balloon and adjusts the pressure using the method described hereinabove for the more basic embodiment. The syringe and gauge are then removed and the inflation check valve 28 closes. With this embodiment, a patient pump 120 with reservoir and preset pressure regulating valve is provided. Such a pump is shown in FIG. 10.

The physician fills the pump and reservoir with sterile fluid and connects the pump to the inflation check valve for the expander balloon. A male Luer Lock fitting affixed to the pump engages the female Luer hub on the check valve. The physician squeezes the pump bulb and the expander intraluminal pressure is established by the pump regulating valve. The patient is instructed to periodically squeeze the pump to maintain the intraluminal pressure on the expander balloon. The preset regulation feature of the pump prevents over pressurizing.

The preset patient pump is shown in FIG. 10, generally indicated at 120 and consists of an elastomeric pump bulb 82, that may double as a reservoir, which is joined to a valve segment 84 containing two valves 86 and 88. A single tube 90 emanates from the valve segment and terminates at a male Luer Lock fitting 92 (not shown but similar to FIG. 9). The pump includes a pressure regulation feature which is set at the factory.

Pump Bulb—82:

The pump bulb 82 is preferably a molded elastomer such as latex, silicone, polyurethane, EPDM or C-Flex, preferably silicone. The fluid volume may vary but is anticipated to be on the order of about 10–20 milliliters.

Valve—86:

Valve 86 is located in the fluid path between the pump bulb 82 and the tubing 90. The valve consists of an elastomeric valve seat 86a, check ball 86b and compression spring 86c. The ball preferably is about 0.125" in diameter and the spring is about 0.125" outside diameter with a length of approximately 0.31". The ball 86b and spring 86c may be fabricated from AISI 304 if sterile water is used, or a cobalt, nickel, molybdenum and chrome alloy if a saline solution is used. Both metals are commercially available from several sources domestically. Valve 86 is oriented as a spring-loaded check valve, so that when the pump bulb 82 is squeezed, fluid will flow from the pump bulb through valve 86 and into the tubing 90. Pump valve 86 prevents fluid flow in the reverse direction from tubing 90 to the pump bulb 82.

Valve—88:

Valve 88 uses the same type of ball and spring as valve 86, and has a similar valve seat 88a, ball 88b and spring 88c. This valve is oriented so that it functions as a preset pressure regulating valve. This valve is also located in a fluid path between the pump bulb 82 and tubing 90. When the pump bulb is squeezed, the regulating valve 88 remains closed and fluid is prevented from flowing from the pump bulb to the tubing. When the pump bulb is released, pressure in the tubing 90 and expander balloon 18 in excess of the pressure setting of the regulating valve, is vented from the tubing 90 through valve 88 to the pump bulb 82.

The valve segment housing 84 valves 86 and 88 are fabricated from an elastomer, preferably silicone. As is known in the valve art, the springs may be selected to provide predetermined or preset regulation based on their strength.

Pump Tubing—90:

The pump tubing 90 connects the pump valve segment 84 to the male Luer Lock fitting 92, and provides a flexible fluid conduit so that the pump may be remote from the proximal end of the expander device 10. The tubing is elastomer, preferably silicone. The tubing preferably has a bore of about 0.031 to 0.062 inch, with a wall thickness equal to or greater than about 50% of the bore. The tubing may be molded integral with the valve segment 84 or extruded and subsequently bonded to it.

Luer Lock—92: (See FIG. 9 for similar arrangement)

A male Luer Lock 92 having a 6% taper is affixed to the end of the tubing 90 with a compression collar 94. The Luer fitting and collar are fabricated from either metal or thermoplastic, and are available from several domestic sources. The male Luer Lock is sized per ANSI/HIMA MD 70.1 (incorporated herein by reference) to engage a female Luer taper and hub on the expander inflation check valve 28.

MEASURING PROCEDURE

An anesthetic sterile lubricating jelly is inserted into the urethra a few minutes prior to measuring. A cystoscope sheath with a minimum bore of 11 French is inserted into the urethra up to the external sphincter. The measuring catheter is passed through the cystoscope bridge sidearm and working channel of the cystoscope sheath and into the bladder. The positioning balloon is then inflated with sterile fluid, to its recommended volume, using a syringe engaged to the check valve. The syringe is then removed which closes the check valve and maintains fluid in the positioning balloon. A gentle traction is applied to the measuring catheter to draw the positioning balloon against the bladder neck. The cystoscope is then used to measure the distance to the external sphincter. When measurement is completed, the positioning balloon is deflated using a syringe engaged to the check valve. The measuring catheter is withdrawn form the cystoscope and the cystoscope is withdrawn form the urethra.

PROSTATE EXPANSION PROCEDURE WITH PATIENT PUMP

After the prostatic urethra is measured to determine the distance from the bladder neck to the external sphincter, an expander 10 of appropriate size is selected. An anesthetic lubricating jelly is inserted into the urethra. The expander is coated with jelly and inserted through the urethra and into the bladder. A syringe filled with sterile fluid is connected to the inflation check valve 24 for the positioning balloon 16. The balloon is inflated to the recommended volume and the syringe is disengaged to close check valve 24. A gentle traction is applied to the expander catheter shaft to urge the positioning balloon against the bladder neck. With a palpating index finger in the rectum, the physician can determine if the nodule 62 is at the apex of the prostate, which indicates correct sizing of the expander. While maintaining gentle traction on the positioning balloon, the expander balloon 18 is inflated. To fill the expander the physician uses a syringe with sterile fluid and engages it to the Luer fitting on the check valve 28 for the expander balloon. The syringe is equipped with a pressure gauge to indicate the intraluminal pressure of the expander balloon. Fluid should be introduced into the expander and withdrawn several times, with the external sphincter positioned superior to the prostate, to evacuate any air. The physician then inflates the expander to recommended pressure; checks the fit of the expander after inflation by palpating the locating nodule 62; and disengages the syringe which closes the expander balloon check valve 28.

When the physician uses a patient pump (FIG. 10), it is filled with sterile fluid and connected to the expander balloon check valve 28. An appropriate Luer Lock fitting on the pump tube secures the pump to check valve 28. The pump bulb is squeezed and the expander is inflated to the predetermined pressure.

Alternatively, if the embodiment (pump FIG. 9) with optional adjustable regulator valve is used, the physician uses a Luer adapter to attach the syringe and gauge to the pump. The optional adjustment tool 100 is then inserted through the pump bulb and into the adjustment screw 104 on the regulating pump valve 88. The physician then applies fluid pressure with the syringe and observes the pressure required to open the regulating valve 88. The regulating pressure is then adjusted by turning the adjustment screw 104 to either increase or decrease the pressure of the regulating valve 88. The adjustment tool is withdrawn and the pump is filled and the syringe and Luer adapter are disconnected. The pump is then secured to check valve 28 using an appropriate Luer Lock fitting which may be provided on the pump tubing. The physician squeezes the pump bulb and the expander is inflated to the physician determined pressure. The patient is instructed to periodically squeeze the pump bulb to maintain the desired intraluminal pressure on the expander balloon. Periodic squeezing of the pump bulb will replenish fluid lost to osmosis, restore fluid pressure which may have been depleted due to tissue expansion, or physiologically induced pressure spikes which may have caused regulating valve 88 to activate.

Optimum expander balloon intraluminal pressure will vary. However, it is anticipated that the pressure range will be 1-½ to 10 psi. ASTM standard for soft tissue expanders requires that the injection site septums not leak when tested with 120 mm Hg (2.32 psi). Previous testing of prior art tissue expander injection sites resulted in leakage around 5 psi, which would indicate tissue expansion occurs below 5 psi. Maximum urethral pressure from urine flow is reported to be 100 cm $H_2O$ which is 1.42 psi.

Various modifications can be made to the present invention without departing from the apparent scope hereof.

What is claimed is as follows:

1. A prostatic tissue expander which may be inserted through the urethra of a patient having a prostate for the purpose of exerting pressure on and expanding said prostate to an expanded condition, said prostatic tissue expander being inserted within said urethra of said patient during an insertion procedure and remaining indwelling within said patient for an extended period of time on the order of about one day or more while said patient engages in a substantially normal range of daily activities, said prostatic tissue expander comprising:

a catheter for insertion at least partially within the urethra of the patient, said catheter having a distal end and a proximal end, said catheter including an expansion member operatively connected to said catheter, said expansion member being inflatable and capable of expanding a predetermined amount to exert the pressure on the prostate generally radially outward against the prostate and maintaining the pressure for the extended period of time as the prostate adapts to the expanded condition, said expansion member being maintained in proper position within the prostate throughout the extended period of time; and an expansion control mechanism operatively connected to and carried on the catheter for selectively controlling the expansion of the expansion member, at least a portion of said expansion control mechanism remaining connected to said catheter subsequent to the insertion procedure for the extended period of time while the patient engages in the substantially normal range of daily activities and the prostate adapts to the expanded condition.

2. The method of claim 1 wherein expansion of the prostatic tissue is gradual and accomplished in a plurality of successive inflation increments over the extended period of time.

3. The method of claim 2 wherein the plurality of successive increments includes selectively and progressively increasing the pressure exerted on the prostatic tissue by the inflatable tissue expander.

4. The method of claim 2 wherein the plurality of successive increments includes selectively increasing or decreasing the pressure exerted on the prostatic tissue by the inflatable tissue expander.

5. The method of claim 2 wherein the plurality of successive increments includes selectively and progressively decreasing the pressure exerted on the prostatic tissue by the inflatable tissue expander.

6. The method of claim 1 wherein the patient has a bladder containing urine and the method further comprises the step of:

draining urine from the bladder of the patient during the extended period of time when the expansion member is expanding the prostatic tissue.

7. A method for expanding a prostatic tissue in a patient having a urethra, a prostate, and a bladder, said bladder having a neck, said method comprising the steps of:

inserting a catheter having a proximal end and a distal end, a positioning balloon, and an expansion balloon into the urethra of the patient until said distal end of said catheter and said positioning balloon are disposed at least partially within the bladder;

inflating said positioning balloon;

applying traction to said catheter to draw said positioning balloon generally proximally toward and against the neck of the bladder such that said expansion balloon is positioned at least partially within and surrounded by the prostate;

inflating said expansion balloon positioned at least partially within the prostate to an inflated configuration such that said expansion balloon exerts a pressure upon the prostatic tissue to expand the prostatic tissue to an expanded condition; and maintaining the expansion balloon in said inflated configuration over an extended period of time on the order of about one day or more during which the prostatic tissue adapts to said expanded condition and the patient engages in a substantially normal range of daily activities.

8. The method of claim 7 wherein the patient has a bladder containing urine and the method further comprises the step of:

draining urine from the bladder of the patient during the extended period when the expansion member is expanding the prostatic tissue.

9. The method of claim 7 further comprising the step of:

maintaining the positioning balloon in the inflated configuration over the extended period of time during which the prostatic tissue adapts to said expanded condition and the patient engages in a substantially normal range of daily activities.

10. A method for expanding a prostatic tissue in a patient having a urethra and a prostate, said method comprising the steps of:

inserting at least a portion of an inflatable tissue expander into the urethra of the patient such that said portion of said inflatable tissue expander is positioned within the prostate adjacent the prostatic tissue to be expanded;

actuating said inflatable tissue expander to an expanded configuration so as to exert a pressure upon the prostatic tissue, said pressure being sufficient to expand the prostatic tissue to an expanded condition without substantial trauma to the urethra or the prostate; and maintaining said pressure on the prostatic tissue over an extended period of time on the order of about one day or more by retaining said inflatable tissue expander in said expanded configuration while the patient continues to engage in a substantially normal range of daily activities and the prostatic tissue adapts to said expanded condition during the extended period of time.

11. The method of claim 10 wherein the patient has a bladder containing urine, and wherein the method further comprises the step of:

periodically draining the urine from the bladder of the patient while the tissue expander remains in the expanded configuration exerting the pressure on the prostatic tissue.

12. The method of claim 10 further comprising the step of:
providing the inflatable tissue expander, the inflatable tissue expander having a catheter adapted to be inserted through the urethra of the patient, said catheter having a distal end and defining an inflation lumen, an expansion balloon operatively connected to said catheter generally proximate to said distal end and fluidly communicating with said inflation lumen, and an expansion control mechanism operatively connected to said catheter and capable of maintaining and selectively increasing or decreasing the pressure exerted on the prostatic tissue by the expansion balloon.

13. The method of claim 10 further comprising the step of:
providing the inflatable tissue expander, the inflatable tissue expander having a catheter body, an inflatable expansion member connected to and carried on said catheter body, and an expansion control mechanism operatively connected to said inflatable expansion member, said expansion control mechanism including a pump and a valve, said pump being actuated to increase the pressure exerted on the prostatic tissue by the inflatable expansion member, said valve maintaining the pressure exerted on the prostatic tissue by the expansion member when said pump is not being actuated.

14. The method of claim 13 wherein the step of providing the inflatable tissue expander includes providing the inflatable tissue expander in which the expansion control mechanism includes a pressure regulator, said pressure regulator being a relief valve preventing the pressure exerted by the expansion member on the prostatic tissue from exceeding a predetermined relief pressure when the pump is actuated.

15. The method of claim 14 wherein the step of providing the inflatable tissue expander includes providing the inflatable tissue expander in which the pressure regulator may be selectively adjusted so as to incrementally increase or decrease the predetermined relief pressure.

16. The method of claim 14 wherein the step of providing the inflatable tissue expander includes providing the inflatable tissue expander in which the pressure regulator may be selectively adjusted using a tool, said tool being separate and operatively removable from the expansion control mechanism, whereby the patient may be prevented from selectively adjusting the predetermined relief pressure by removing the tool.

17. The method of claim 13 wherein the step of providing the inflatable tissue expander includes providing the inflatable tissue expander in which the pump may be selectively disconnected from the catheter and selectively reconnected to the catheter, the valve maintaining the desired pressure within the inflatable expansion member when the pump is disconnected from the catheter.

18. The method of claim 13 wherein the step of providing the inflatable tissue expander includes providing the inflatable tissue expander in which the expansion control mechanism includes a pressure regulator, said pressure regulator preventing the pressure exerted by the inflatable expansion member on the prostatic tissue from exceeding a predetermined maximum applied pressure when the pump is actuated.

19. The method of claim 18 wherein the step of providing the inflatable tissue expander includes providing the inflatable tissue expander in which the pressure regulator may be selectively adjusted so as to incrementally increase or decrease the predetermined maximum applied pressure.

20. The method of claim 18 wherein the step of providing the inflatable tissue expander includes providing the inflatable tissue expander in which the pressure regulator may be selectively adjusted using a tool, said tool being separate and operatively removable from the expansion control mechanism, whereby the patient may be prevented from selectively adjusting the predetermined maximum applied pressure by removing the tool.

21. A method for expanding a prostate in a patient having a urethra at least partially occluded due to pressure from said prostate, said method comprising the steps of:

providing an expansion member;

inserting at least a portion of said expansion member into the urethra of the patient such that said portion of said expansion member is positioned within the interior portion of the prostate to be expanded;

actuating the expansion member to an expanded configuration so as to exert a pressure outwardly upon the prostate, said pressure being sufficient to expand the prostate to an expanded condition such that the urethra is no longer occluded, and without causing substantial trauma to the urethra or the prostate;

maintaining said pressure on the prostate over an extended period of time on the order of about one day or more by retaining said expansion member within the prostate in said expanded configuration sufficient to effect expansion of the prostate while the patient continues to engage in a substantially normal range of daily activities and the prostate gradually adapts to said expanded condition during the extended period of time;

retracting said expansion member from said expanded configuration at the conclusion of said extended period of time; and removing said expansion member from within the tissue body and the channel of the patient.

22. The method of claim 21 wherein the expansion member further includes an inflatable expansion balloon connected to and carried on a catheter, and an expansion control mechanism operatively connected to said catheter, said expansion control mechanism including a pump having a valve, and wherein the actuating step further comprises the step of:

selectively actuating the pump to increase the pressure exerted on the prostate by the inflatable expansion balloon, the valve maintaining the pressure exerted on the prostate by the inflatable expansion balloon when the pump is not being actuated.

* * * * *